US009398979B2

(12) United States Patent
Hohla et al.

(10) Patent No.: US 9,398,979 B2
(45) Date of Patent: Jul. 26, 2016

(54) DIMENSIONAL COMPENSATOR FOR USE WITH A PATIENT INTERFACE (71) Applicant: Technolas Perfect Vision GmbH, Munich (DE)

(72) Inventors: Kristian Hohla, Munich (DE); Frieder Loesel, Mannheim (DE); Gwillem Mosedale, Munich (DE); Gerhard Youssefi, Landshut (DE)

(73) Assignee: Technolas Perfect Vision GmbH, Munich (DE)

( * ) Notice: Subject to any disclaimer, the term of this patent is extended or adjusted under 35 U.S.C. 154(b) by 63 days.

(21) Appl. No.: 13/793,396

(22) Filed: Mar. 11, 2013

(65) Prior Publication Data
US 2014/0257256 A1 Sep. 11, 2014

(51) Int. Cl.
*A61F 9/008* (2006.01)
*A61F 9/009* (2006.01)

(52) U.S. Cl.
CPC ............ *A61F 9/008* (2013.01); *A61F 9/009* (2013.01); *A61F 9/00825* (2013.01); *A61F 2009/00848* (2013.01); *A61F 2009/00851* (2013.01); *A61F 2009/00872* (2013.01)

(58) Field of Classification Search
USPC ........................................................ 606/2–6
See application file for complete search history.

(56) References Cited

U.S. PATENT DOCUMENTS

| 4,452,506 A | 6/1984 | Reeve et al. |
| 4,474,423 A | 10/1984 | Bisbee et al. |
| 4,812,641 A | 3/1989 | Ortiz, Jr. |
| 4,838,631 A | 6/1989 | Chande et al. |
| 4,905,711 A | 3/1990 | Bennett et al. |
| 4,907,872 A | 3/1990 | Schirmer et al. |
| 5,098,426 A | 3/1992 | Sklar et al. |
| 5,108,412 A | 4/1992 | Krumeich et al. |

(Continued)

FOREIGN PATENT DOCUMENTS

| CA | 2735264 A1 | 8/2008 |
| EP | 1364632 A1 | 11/2003 |

(Continued)

OTHER PUBLICATIONS

Wyant et al, Basic Wavefront Aberration Theory for Optical Metrology, Applied Optics and Optical Engineer, vol. XI, Chapter 1, pp. 1-53.*

*Primary Examiner* — Lynsey Crandall
*Assistant Examiner* — Qingjun Kong
(74) *Attorney, Agent, or Firm* — Nydegger & Associates (57) ABSTRACT An apparatus and method are provided for performing ocular laser surgery using a patient interface having a posterior contact surface that may include surface irregularities that were generated during manufacturing of the patient interface. A beam delivery system having a focusing lens, scanning subsystem and adaptive optic (e.g. deformable mirror) is provided for guiding the surgical laser beam through the patient interface and to a desired focal spot location. An optical detector generates image data representing the posterior patient interface surface which is then processed by a computer system to identify surface irregularities by comparing the image data to a reference surface or axis. In particular, a surface irregularity can be identified as having a z-axis component; a tilt component and a surface profile component. Each irregularity component can be compensated separately by sending an adjustment signal to one of the beam delivery system components.

10 Claims, 4 Drawing Sheets

(56) References Cited

U.S. PATENT DOCUMENTS

| | | |
|---|---|---|
| 5,159,361 A | 10/1992 | Cambier et al. |
| 5,281,211 A | 1/1994 | Parel et al. |
| 5,336,215 A | 8/1994 | Hsueh |
| 5,493,109 A | 2/1996 | Wei et al. |
| 5,549,632 A | 8/1996 | Lai |
| 5,620,436 A | 4/1997 | Lang et al. |
| 5,779,696 A | 7/1998 | Berry et al. |
| 5,865,832 A | 2/1999 | Knopp et al. |
| 6,004,314 A | 12/1999 | Wei et al. |
| 6,091,074 A | 7/2000 | Korevaar |
| 6,097,522 A | 8/2000 | Maerki et al. |
| 6,099,522 A | 8/2000 | Knopp et al. |
| 6,143,011 A | 11/2000 | Hood et al. |
| 6,322,556 B1 | 11/2001 | Gwon et al. |
| 6,325,792 B1 | 12/2001 | Swinger et al. |
| 6,373,571 B1 | 4/2002 | Juhasz et al. |
| 6,454,761 B1 | 9/2002 | Freedman |
| 6,485,413 B1 | 11/2002 | Boppart et al. |
| 6,497,701 B2 | 12/2002 | Shimmick et al. |
| 6,702,809 B1 | 3/2004 | Knopp et al. |
| 6,726,680 B1 | 4/2004 | Knopp et al. |
| 6,730,074 B2 | 5/2004 | Bille et al. |
| 6,751,033 B2 | 6/2004 | Goldstein et al. |
| 6,787,733 B2 | 9/2004 | Lubatschowski et al. |
| 6,863,667 B2 | 3/2005 | Webb et al. |
| 6,913,603 B2 | 7/2005 | Knopp et al. |
| 6,966,905 B2 | 11/2005 | Bille |
| 7,018,376 B2 | 3/2006 | Webb et al. |
| 7,125,119 B2 | 10/2006 | Farberov |
| 7,371,230 B2 | 5/2008 | Webb et al. |
| 7,390,089 B2 | 6/2008 | Loesel et al. |
| 7,402,159 B2 | 7/2008 | Loesel et al. |
| 7,611,507 B2 | 11/2009 | Raksi et al. |
| 7,692,865 B2 | 4/2010 | Muehlhoff et al. |
| 7,836,892 B2 | 11/2010 | Dick et al. |
| 7,955,324 B2 | 6/2011 | Melcher et al. |
| 7,976,155 B2 | 7/2011 | Muehlhoff et al. |
| 8,088,124 B2 | 1/2012 | Loesel et al. |
| 2001/0041884 A1* | 11/2001 | Frey et al. ............ 606/5 |
| 2002/0173778 A1 | 11/2002 | Knopp et al. |
| 2004/0021874 A1 | 2/2004 | Shimmick |
| 2004/0059321 A1 | 3/2004 | Knopp et al. |
| 2005/0024586 A1 | 2/2005 | Teiwes et al. |
| 2006/0192921 A1 | 8/2006 | Loesel et al. |
| 2007/0173794 A1 | 7/2007 | Frey et al. |
| 2007/0237620 A1 | 10/2007 | Muehlhoff et al. |
| 2008/0078752 A1 | 4/2008 | Bischoff et al. |
| 2008/0183159 A1 | 7/2008 | Preuss et al. |
| 2008/0228176 A1 | 9/2008 | Triebel et al. |
| 2008/0234707 A1 | 9/2008 | Muehlhoff et al. |
| 2009/0069794 A1* | 3/2009 | Kurtz ............... 606/4 |
| 2010/0022994 A1 | 1/2010 | Frey et al. |
| 2010/0274228 A1 | 10/2010 | Mrochen et al. |
| 2011/0022035 A1 | 1/2011 | Porter et al. |
| 2011/0028953 A1* | 2/2011 | Raksi ............... A61F 9/008 606/4 |
| 2011/0102810 A1 | 5/2011 | Bischoff et al. |
| 2011/0202044 A1 | 8/2011 | Goldshleger et al. |
| 2011/0238045 A1 | 9/2011 | Dick et al. |
| 2011/0304819 A1* | 12/2011 | Juhasz ............... A61B 3/102 351/206 |
| 2011/0319873 A1 | 12/2011 | Raksi et al. |
| 2011/0319875 A1* | 12/2011 | Loesel ............ A61F 9/00825 606/4 |
| 2012/0016349 A1 | 1/2012 | Brownell |
| 2012/0078241 A1 | 3/2012 | Gooding et al. |

FOREIGN PATENT DOCUMENTS

| | | |
|---|---|---|
| EP | 1769732 A2 | 4/2007 |
| EP | 1844744 A1 | 10/2007 |
| EP | 2301423 A1 | 3/2011 |
| WO | 9515134 | 6/1995 |
| WO | 0189373 A3 | 11/2001 |
| WO | 2006002392 A2 | 1/2006 |
| WO | 2007127257 A3 | 11/2007 |
| WO | 2009036098 A2 | 3/2009 |
| WO | 2009073502 A2 | 6/2009 |
| WO | 2012041347 A1 | 4/2012 |

* cited by examiner

DIMENSIONAL COMPENSATOR FOR USE WITH A PATIENT INTERFACE

FIELD OF THE INVENTION

The present invention pertains generally to systems and methods for performing ocular surgery using a patient interface. More particularly, the present invention pertains to computer-controlled laser surgical systems. The present invention is particularly, but not exclusively, useful as a system and a method that compensates for manufacturing defects in a patient interface to improve the accuracy of a laser treatment procedure.

BACKGROUND OF THE INVENTION

When using a laser beam to perform ocular surgery, the precise positioning of the laser beam's focal spot at a desired location in the tissue to be altered is important. Specifically, focal spot position accuracies within about ten microns (10 μm) or less are preferable. In addition to focal spot position, beam quality can affect the size and shape of the focal spot. In particular, laser beams with high beam quality are desirable because they can be used to produce relatively small, uniformly shaped focal spots.

For these treatment procedures, it is often desirable to use a patient interface to properly stabilize and align the eye with the surgical laser unit. In many instances, such stabilization may be best accomplished by placing the eye in direct contact with a patient interface of the laser unit. Typically, this involves placing the exterior surface of the cornea in contact with a posterior surface of a contact element (i.e. plate or lens) that is transparent to the surgical laser beam. In some cases, the posterior surface of the contact element may be flat, and, when applied to the cornea may flatten the cornea. Alternatively, the posterior surface of the contact element may be curved and substantially conforming to the exterior surface of the cornea. For this case, when the contact element is applied to the cornea, little or no flattening or distortion of the cornea occurs. In still other cases, a slightly curved contact element may be employed, slightly deforming, but not fully flattening the cornea when applied. Unlike a flat contact element, one advantage of using the curved/conforming contact element is that it does not cause distortions or wrinkles on the anterior surface of the cornea. These distortions or wrinkles can adversely affect a beam passing through the cornea and affect beam quality and focusability for beams used to treat target tissue that is located deeper in the eye than the cornea (e.g. the lens, retina, etc.).

In addition to the contact element, the patient interface typically includes a stabilizing device, such as a suction ring, that can be positioned directly against the eye (e.g. against the cornea) to hold the contact element against the cornea. An interface device can then be engaged with the stabilizing device and is used to fixedly hold the stabilizing device (e.g. the suction ring) relative to the laser unit. For example, U.S. Pat. No. 7,955,324 which issued to Melcher et al. for an invention entitled "Cornea Contact System," and which is assigned to the same assignee as the present invention, discloses a system for this purpose.

Regardless of the type of contact element used (i.e. flat, slightly curved or curved and conforming to the cornea), the surfaces of the contact element have, heretofore, generally been manufactured to high dimensional tolerances. In this regard, variations in surface figure (i.e. shape) from the desired shape, as well as poor surface roughness, can affect a beam passing through the contact element. In the case of a curved contact surface which is generated using a turning technique, it can be relatively expensive to consistently obtain a contact surface that is free of surface irregularities that can affect beam position or beam quality.

Because of the high cost of manufacturing high-precision contact elements they are typically re-used on a number of different patients. Each use, in turn, requires the contact element to be sterilized and re-inspected for defects. This adds undesirable cost and complexity to the treatment procedure. If manufacturing defects could be compensated, lower cost methods of manufacturing contact elements, which do not necessarily involve turning, such as injection molding, may be used. In fact, these methods may lower the cost of manufacturing the contact element sufficient to allow for single use (i.e. disposable) contact elements, eliminating the need (and cost) for sterilization and inspection.

In light of the above, it is an object of the present invention to provide a method and apparatus for directing a surgical laser beam to a treatment area while compensating for the effects of irregularities (e.g. manufacturing defects) on the posterior surface of a patient interface. Another object of the present invention is to provide a method and apparatus which allow a low cost, dimensionally tolerant patient interface to be used in a laser procedure without reducing focal spot positioning accuracy or focusability. Yet another object of the present invention is to provide a method and apparatus which allows for alternative manufacturing methods to be used to produce a patient interface, such as injection molding, without reducing focal spot positioning accuracy or focusability. Still another object of the present invention is to provide a dimensional compensator for use with a patient interface that is easy to implement, is relatively simple to use, and is comparatively cost effective.

SUMMARY OF THE INVENTION

In accordance with the present invention, an apparatus and method are provided for performing ocular surgery using a patient interface (PI). In particular, the patient interface includes an anterior surface and a posterior surface that may include surface irregularities that are generated during manufacturing.

During a treatment procedure, a surgical laser beam is passed through the patient interface to a treatment area within the eye of a patient. As the beam passes through the patient interface, the surface irregularities on the posterior surface of the patient interface can adversely affect the beam position and/or the beam's quality. For the present invention, the surface irregularities on the posterior surface of the patient interface are imaged and compensation is provided to obviate the effects of these irregularities on beam position and beam quality.

In more structural terms, the apparatus can include a beam delivery system for guiding the surgical laser beam along a beam path through the patient interface and to a desired focal spot location in the treatment area. Typically, the beam delivery system includes an optic, such as a focusing lens for adjusting the focal spot position along the direction of beam propagation (i.e. along a z-axis). In addition, the beam delivery system can include a scanning subsystem, for example having one or more tip-tilt mirrors, for steering the focal spot position in directions normal to the z-axis (i.e. x and y axes). Also, the beam delivery system can include an adaptive optic such as an adaptive/deformable mirror for selectively altering the beam's wavefront. In some cases, within the beam delivery system, an optic may be used for more than one of the functions described above. For example, a common optic may be used to both steer and focus the beam, or, a common optic may be used to both steer and alter the beam's wavefront, etc.

In addition to the beam delivery system, the apparatus can include an optical detector that creates image data. For example, the optical detector can include an optical coherence tomography (OCT) detector or some other suitable detector (see below) for producing image data. For the apparatus, the detector produces image data representing the portion of the posterior surface of the patient interface that the laser beam passes through. In most cases, the detector also produces image data representing the treatment area.

For the method and apparatus of the present invention, the image data generated by the optical detector is sent to a computer system which receives and processes the data. In particular, the image data is processed to identify and characterize irregularities that are present on the posterior PI surface. The computer system then outputs one or more adjustment signal(s) that are sent to one or more beam delivery system component(s) to compensate for the surface irregularities.

To identify and characterize the surface irregularities, image data representing a posterior PI surface is compared to a reference datum such as a reference surface or reference axis. This comparison generally yields three surface irregularity components which can be compensated separately. In more detail, the surface irregularity can include a z-axis component, a tilt component and a surface profile component.

For the z-axis component, the image data can be processed to compare the z-axis coordinate where the beam passes through the posterior PI surface to a corresponding z-axis coordinate on a reference model. Specifically, the reference model can be a computer model of a posterior surface of a patient interface having no surface irregularities. For example, a set of coordinates making up a reference model surface can be provided as an input to the computer system prior to the treatment procedure. The calculated difference between the posterior PI surface and the reference model, $\Delta z$, can then be used by the computer system to generate an output signal that is indicative of (e.g. proportional to) the distance, $\Delta z$. The output signal is then sent to the beam delivery system which responds to the signal by moving a beam delivery system component, such as the focusing lens. Specifically, the beam delivery system can move the beam delivery system component through an appropriate distance that will compensate for the z-axis component of the surface irregularity.

To characterize and compensate for a tilt component of a posterior PI surface irregularity, the image data can be processed by the computer system to compare a degree of inclination of the surface portion where the beam passes through the posterior PI surface to a reference datum. For example, the reference datum used for comparison can be a corresponding surface portion on a reference model of a posterior surface of patient interface having no surface irregularities. Alternatively, an axis that is normal to the posterior PI surface can be calculated by the computer system and then compared with a reference axis to calculate the tilt component of the irregularity. For instance, the reference axis may be an anatomical axis of the eye such as the eye's optical axis or visual axis. Once the tilt is determined, the computer system can generate an output signal that is indicative of the tilt and transmit the output signal to the beam delivery system. The beam delivery system can then respond to the signal by moving a beam delivery system component, such as an optic in the scanning system. Specifically, the beam delivery system can move the beam delivery system component by an appropriate increment that will compensate for the tilt component of the surface irregularity.

To characterize and compensate for a surface profile component of a posterior PI surface irregularity, the image data can be processed by the computer system to compare the profile of the surface portion where the beam passes through the posterior PI surface to a reference datum. For example, the reference datum used for comparison can be a corresponding surface portion on a reference model of a posterior surface of patient interface having no surface irregularities. The comparison yields a surface profile deviation due to the surface irregularity. The surface profile deviation associated with the surface irregularity can then be used to estimate a wavefront profile that will be induced by the surface irregularity. A compensating signal can then be generated by the computer system and sent to the beam delivery system. For example, the compensating signal can be configured to cause the adaptive optic of the beam delivery system to induce a wavefront profile on the beam that is equal and opposite to the estimated wavefront profile that will be induced by the surface irregularity.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
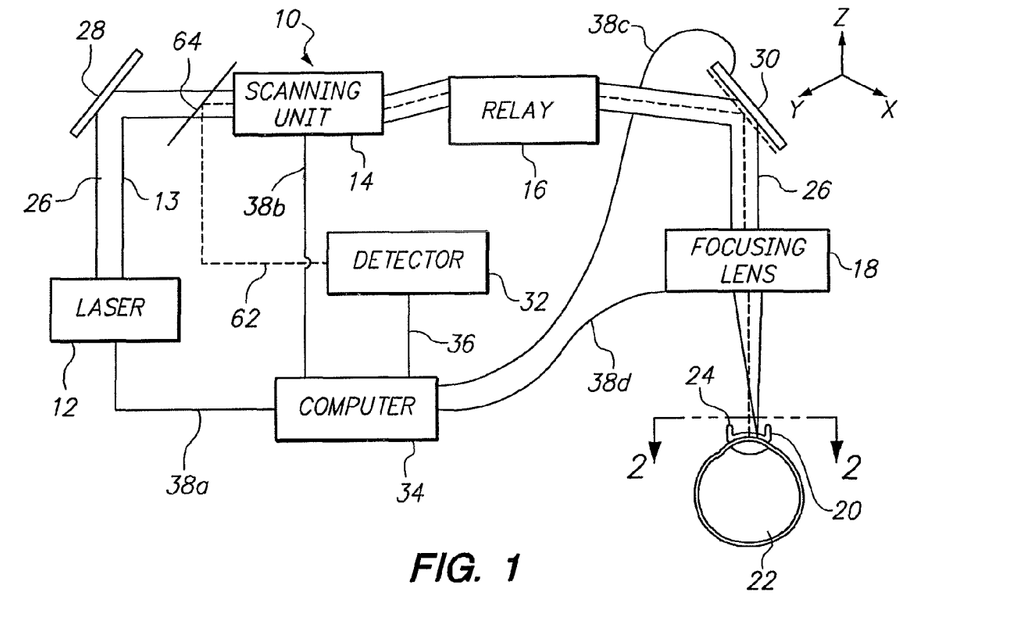
FIG. 1 is a schematic drawing of an apparatus for performing ocular surgery in accordance with the present invention.

Referring initially to FIG. 1, an apparatus for performing ocular surgery in accordance with the present invention is shown and is generally designated 10. As shown, the apparatus 10 includes a laser source 12 for generating a surgical laser beam 13. For example, the laser source 12 can be an ultrafast laser source such as a so-called femtosecond laser source generating a surgical laser beam 13 that can interact with tissue by laser induced optical breakdown (LIOB). Specifically, one or more pulses having a pulse duration below about one picosecond can be delivered onto exposed tissue or to a sub-surface focal spot to incise tissue by LIOB (i.e. cut tissue by moving a focal spot along a single surface) or remove a volume of tissue by LIOB (i.e. by moving a focal spot within a volume having a thickness greater than a single LIOB surface). In some implementations, the pulses of the surgical laser beam 13 can have a wavelength of approximately one thousand nanometers ($\lambda_s$=1,000 nm).

FIG. 1 also shows that the apparatus 10 can include a scanning subsystem 14 that will allow the surgical laser beam 13 to be moved (i.e. steered) in directions (i.e. x and y directions) that are orthogonal to the direction of beam propagation (i.e. the z direction). For example, the scanning subsystem 14 can include one or more tip-tilt mirrors (not shown) that are driven by one or more actuator(s) (not shown) such as piezoelectric actuator(s).

It can also be seen from FIG. 1 that the apparatus 10 can include a focusing optic, such as a lens 18, that can be used to focus the surgical laser beam 13 to a focal spot 20 in the tissue of a patient's eye 22. Typically, for the apparatus 10, the lens 18 is mounted on a mechanism (not shown) allowing the lens 18 to be moved in the direction of beam propagation to vary the position of the focal spot along a z direction. For example, the movement of the lens 18 can be driven by an actuator (not shown) such as a piezoelectric actuator.

For the present invention, the apparatus 10 can include a patient interface 24 that is held in place against the eye 22, as shown in FIG. 1.

FIG. 1 also shows that the apparatus 10 can include an adaptable optic 30 that is operable on the beam and adjustable to vary a wavefront profile of the beam. For example, the adaptive optic can be an adaptive/deformable mirror such as a multi-faceted mirror in which the position along the beam path of each facet is individually driven by an actuator (not shown) such as a piezoelectric actuator. It is to be appreciated that other types of adaptable optics known in the pertinent art and capable of controllably adjusting the wavefront profile of a laser beam can be used in place of the deformable mirror shown.

Together, the scanning subsystem 14, adaptable optic 30 and focusing lens 18 constitute a beam delivery system which directs the surgical laser beam 13 along a beam path 26 as it progresses from the laser source 12, through the patient interface 24 and ultimately to its focal spot 20 in the eye 22. For this purpose, as shown in FIG. 1, an optional turning mirror 28 and optional relay optics 16 can be provided to transfer the surgical laser beam 13 along a beam path in a manner well known in the pertinent art.

Still referring to FIG. 1, it will be seen that the apparatus 10 can include an optical detector 32 for generating image data. Also, the apparatus 10 can include a computer system 34 for receiving input data and computer readable instructions, processing computer readable instructions including instructions which operate on stored data, and output control signals and/or data for display purposes. For example, the computer system may include a personal computer (PC) having standard I/O connections.

For the apparatus 10, the computer system 34 is connected via a line 36 to the optical detector 32 allowing the computer system 34 to control the operation of the optical detector. Further, this connection allows image data generated the optical detector 32 to be transmitted to the computer system 34. It can further be seen that the computer system 34 is connected to the laser source 12 via a line 38a, the scanning subsystem 14 via a line 38b, the adaptable optic 30 via a line 38c and the focusing lens 18 via a line 38d. With these connections, the computer system 34 can transmit control signals to (see further discussion below), and in some cases received data from, the laser source 12 and other components of the apparatus 10.

Continuing with FIG. 1, it can be seen that a diagnostic laser beam (represented by the dotted line 62 in FIG. 1) from the optical detector 32 can be coupled to common beam path 26 with the surgical laser beam 13, for example, using a dichroic mirror 64 that is located upstream from the scanning subsystem 14. In this case, the optical detector 32 can use the same scanning subsystem 14 and focusing lens 18 that is being used for the surgical laser beam 13. As an operational consideration, the diagnostic laser beam 62 can have a wavelength of approximately one thousand three hundred nanometers ($\lambda_d$=1,300 nm). Alternatively, the diagnostic laser beam 62 can be introduced onto the beam path 26 downstream of the scanning subsystem and/or focusing lens 18 configuration or separate beam paths may be used for the diagnostic laser beam 62 and surgical laser beam 13. In these latter cases, the optical detector 32 can include an integral scanning and focusing system.

As envisioned for the present invention, and stated above, the optical detector 32 can use optical coherence tomography (OCT) techniques to create image data of the eye 22 and the patient interface 24. In some cases, the image data can include specific anatomical features of the eye 22 such as a treatment area within which the surgical laser beam will interact with tissue. With this in mind, one method for imaging the interior of an eye involves optical coherence tomography (OCT) techniques. More details regarding OCT equipment and techniques can be found in U.S. Pat. No. 6,004,314 which issued to Wei et al. for an invention entitled "Optical Coherence Tomography Assisted Surgical Apparatus". Alternatively, or in addition to the OCT detector, the apparatus 10 can include one or more other optical detectors such as a confocal imaging detector, a Scheimpflug principle imaging detector, a two photon imaging detector or a second harmonic generation imaging detector.

The image data produced by the optical detector 32 can be processed by the computer system 34 to control one or more aspects of a surgical procedure, and in some cases, can be used to generate human perceptible image views during a procedure for use by the operator.

Typically, the optical detector creates image data that is organized along planes. The planes of data can then be used alone (i.e. a single plane of image data) or multiple planes of data can be combined together, for example, using computer data processing to generate a three dimensional dataset. Moreover, the optical detector can update (i.e. refresh) the image data for a particular plane or plane(s) at predetermined intervals during a procedure, and particularly, can refresh the image data for one or more image planes after each laser firing.

Figures 2, 3:
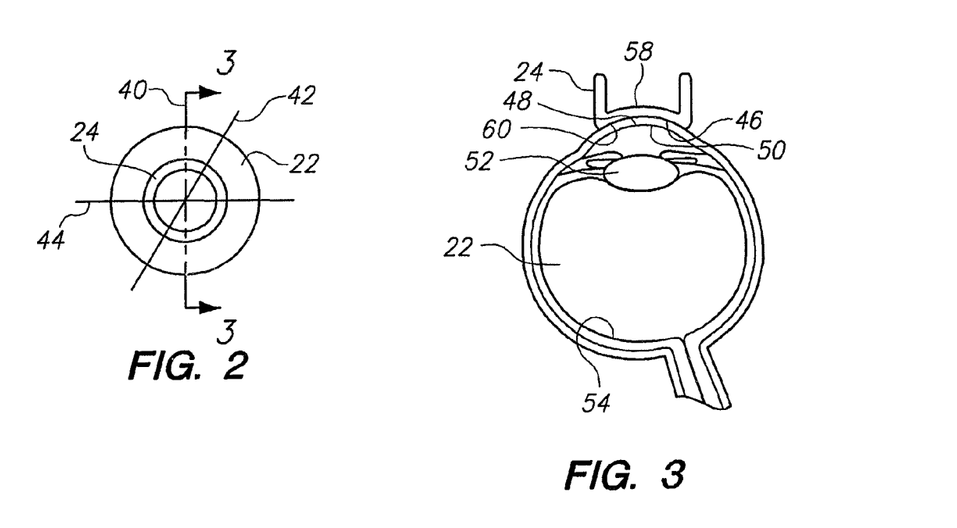
FIG. 2 is a top plan view of an eye as would be seen along the line 2-2 in FIG. 1.
FIG. 3 is a cross-section view of an eye as seen along the line 3-3 in FIG. 2.

In FIG. 2, the eye 22 and patient interface 24 are seen in a top plan view; and end-on indications of several image planes 40, 42 and 44 are shown. Although these image planes 40, 42, and 44 are shown to be generally parallel to the optical axis of the eye 22 and extending into the eye 22, it is to be appreciated that other image plane orientations are achievable with the above-described optical detectors 32 and usable for the purposes described herein.

FIG. 3 shows a cross section view through the eye 22 and patient interface 24 and illustrates a rendering (i.e. view) of image data for the plane 40 shown in FIG. 2. As indicated above, image data from multiple planes, (e.g. OCT data) can be collectively assembled to establish a three-dimensional dataset for representing portions or all of the interior of the eye 22 and patient interface 24. As discussed in more detail below, the three-dimensional dataset can include image data representing a surface of interest such as the posterior surface 60 of the patient interface 24. With this in mind, FIG. 3 illustrates several anatomical features of the eye 22. These include: the anterior surface 46 of the cornea 48, the posterior surface 50 of the cornea 48, the crystalline lens 52, and the retina 54. At this point it is to be noted that less than an entire plane of image data (e.g. as shown in FIG. 3) can be used for the purposes of the present invention. For example, image data corresponding to only a portion of the patient interface 24 may be sufficient as input to the computer system 34 to perform a particular function.

The image plane of FIG. 3 also shows the details of the patient interface 24. In particular, the patient interface 24 includes an anterior surface 58 and an opposed posterior surface 60 that is held in contact with the anterior surface 46 of the cornea 48 during a treatment procedure. As indicated above, the posterior surface 60 of the patient interface 24 may be curved to conform with the anterior surface 46 of the cornea 48 (as shown) or may be flat (not shown) or slightly curved (not shown). On the other hand, the posterior surface 60 is typically either flat or has a curvature that conforms with the curvature of the anterior surface 46. One or both of the anterior surface 58 and posterior surface 60 may include surface defects, that may, for example, be generated during manufacturing or during handling of the patient interface, etc. For clarity purposes, the discussion below will center on compensating for surface defects on the posterior surface 60 with the understanding that the discussion is equally applicable to surface defects/surface variations on any other imagable surface that the laser beam passes through, including the anterior surface 58.

Operation

Figure 4:
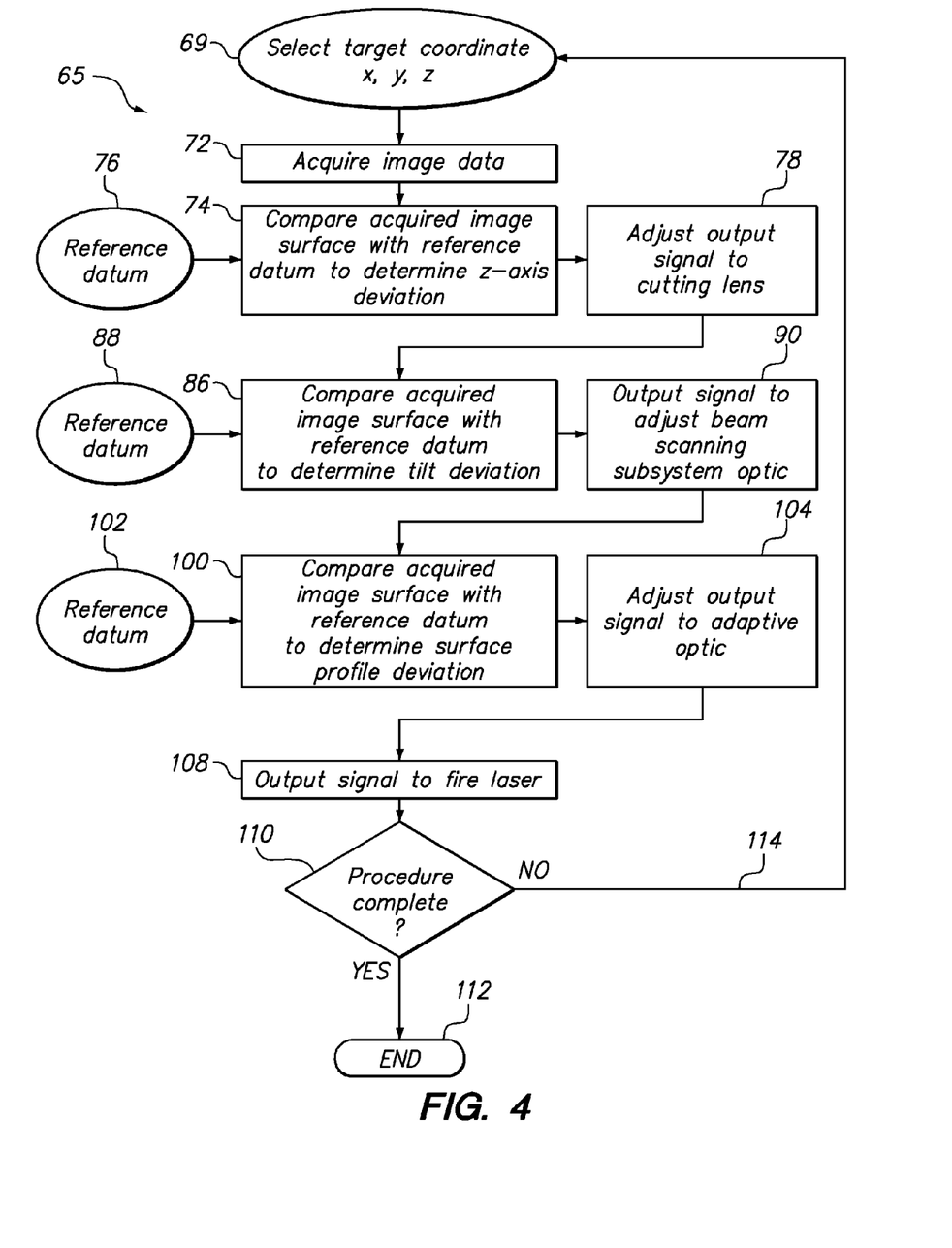
FIG. 4 shows a sequence of steps for performing a surgical treatment on tissue of a patient's eye in accordance with the present invention.

FIG. 4 shows a sequence of steps, generally designated 65 for performing a surgical treatment on targeted tissue of a patient's eye with the surgical laser beam 13 that is generated by the apparatus 10 shown in FIG. 1. It is to be appreciated that the steps and sequence of steps shown in FIG. 4 can be programmed into computer readable instructions, stored in a computer medium, and executed by the computer system 34, described above and shown in FIG. 1, to perform the treatment described herein.

Figure 5:
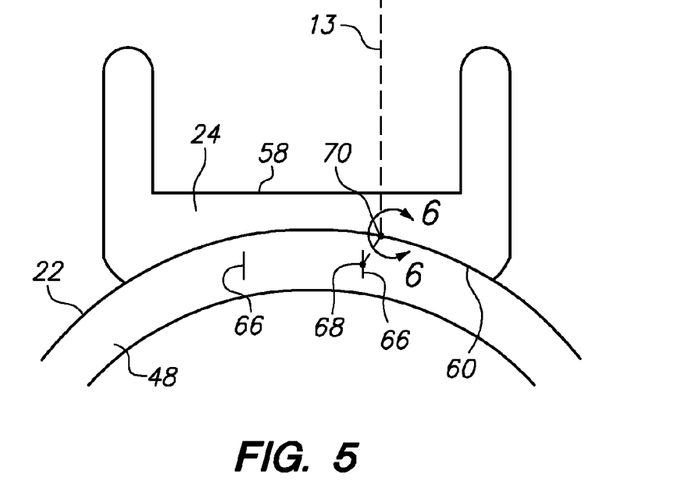
FIG. 5 is an enlarged cross-section view of the cornea of the eye and patient interface shown in FIG. 3.

As shown in FIG. 4, the treatment procedure can begin by selecting a target location, e.g. having coordinates (x, y, z) in the eye, in accordance with a desired treatment plan (Step 69). As shown in FIG. 5, the treatment plan can include the identification of a predetermined path 66 for the focal spot 20 (see FIG. 1) of surgical laser beam 13. FIG. 5 shows an example of a treatment plan having a path 66 that produces a cylindrical incision in the stroma of a cornea 48 of an eye 22. It is to be appreciated that the treatment plan could include other types and shapes of tissue incisions and/or the removal of one or more volumes of tissue.

For the treatment plan shown in FIG. 5, the path 66 can be subdivided into a number of discrete locations along the path 66 such that when LIOB is performed at each discrete location, a continuous cut or incision will be established. For purposes of clarity, the LIOB of location 68 on path 66 will be described with the understanding that the foregoing discussion is applicable to the other locations on the path 66.

FIG. 5 illustrates, for discussion purposes, a posterior surface 60 of a patient interface 24 that does not have any surface irregularities. For the perfect posterior surface 60, the surgical laser beam 13 travels through the patient interface 24 including location 70 on the posterior surface 60 of the patient interface 24 to reach the target location 68.

Figure 6:
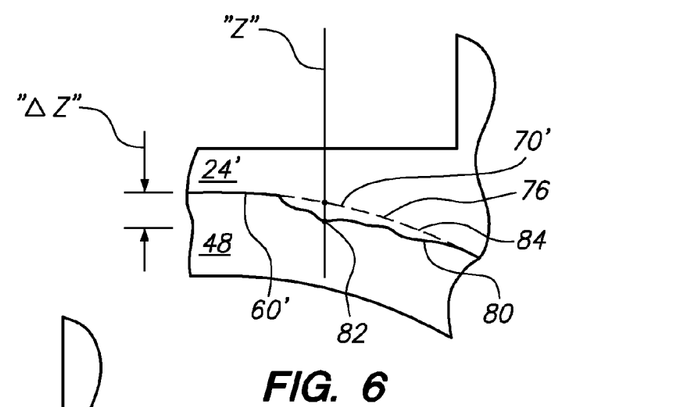
FIG. 6 is an enlarged detail view of a cornea of the eye and a patient interface having a surface irregularity (shown exaggerated for clarity purposes) as enclosed by detail line 6-6 in FIG. 5 and illustrating the measurement of a z-axis component of the surface irregularity for compensation purposes.

FIG. 6 shows a portion of a cornea 48 and patient interface 24' having a surface irregularity 80 on the posterior surface 60'. Note, the size and shape of the surface irregularity 80 has been grossly exaggerated to facilitate discussion. Image data representing the surface irregularity 80 can be acquired by the optical detector 32 (FIG. 1) in Step 72 (FIG. 4).

FIG. 6 also shows a reference datum 76 consisting of a computer model of a posterior surface 84 (illustrated by dashed line) having no surface irregularities. For example, a set of coordinates making up a reference model surface 84 can be provided as an input to the computer system 32 (see FIG. 1) prior to the treatment procedure.

As further shown in FIG. 6, a z-axis component of the surface irregularity 80 can be compared to the reference datum 76 for compensation purposes (Step 74 in FIG. 4). In particular, as shown in FIG. 6, the image data can be processed to compare the z-axis coordinate for location 70' on a reference datum 76 with a corresponding z-axis coordinate for location 82 on the posterior surface 60' to obtain a z-axis deviation, $\Delta z$.

To calculate the z-axis deviation, $\Delta z$, the coordinates of the location 70' can be first ascertained as the position on the reference model surface 84 where a laser beam directed to location 68 would pass. In particular, the location 70' can be calculated based on the shape of the reference model surface and the indices of refraction of the patient interface 24 and cornea 48. Next, with the coordinates of the location 70' identified, the coordinates of location 82 can then be determined. Specifically, the coordinates of location 82 can be identified as the location on the posterior surface 60 and along the z-axis from the location 70'. With the coordinates of location 70' and location 82 identified, the distance, $\Delta z$, between location 70' and location 82 along the z-axis can be calculated. An output signal (FIG. 4; Step 78) indicative of the distance, $\Delta z$, can then be sent to the beam delivery system which responds to the signal by moving a beam delivery system component, such as the focusing lens 18 (FIG. 1). Specifically, the focusing lens 18 can be moved through an appropriate distance that will compensate for the z-axis component of the surface irregularity 80.

Figure 7:
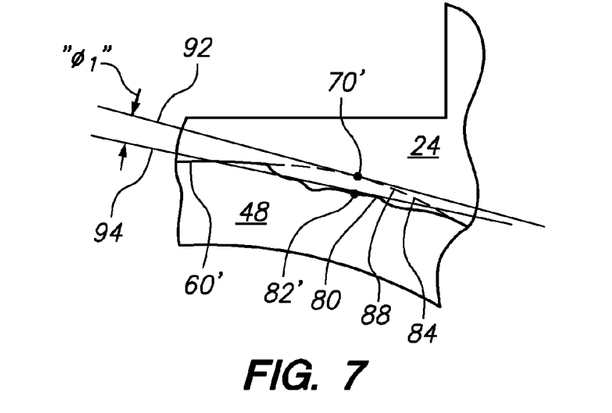
FIG. 7 is an enlarged detail view of a cornea of the eye and a patient interface having a surface irregularity as in FIG. 6 illustrating the measurement of a tilt component of the surface irregularity and the comparison of the tilt component to a corresponding surface on a reference model for compensation purposes.

FIG. 4 also shows (Step 86) that the acquired image data can be compared to a reference datum 88 to characterize and compensate for a tilt component of a surface irregularity 80 (see FIG. 7). Once characterized, the tilt component can be used to generate an output signal for adjusting an optic of the scanning subsystem 14 (FIG. 1) to compensate for the tilt (Step 90).

FIG. 7 shows a first implementation for characterizing tilt using a reference model surface 84 as the reference datum 88. As described above with reference to FIG. 6, the location 70' can be first ascertained as the position on the reference model surface 84 where a laser beam directed to location 68 (FIG. 5) would pass. Next, with the coordinates of the location 70' identified, the coordinates of a corresponding location 82' on the posterior surface 60' can then be determined. Specifically, the coordinates of location 82' can be identified as the location on the posterior surface 60 and along the z-axis (see FIG. 6) from the location 70'. Alternatively, it can be selected to be the nearest point on posterior surface 60' to the location 70' or some other suitable technique can be used to identify the coordinates of the corresponding location 82'.

Continuing with FIG. 7, once the coordinates of location 70' and location 82' have been identified, the degree of inclination at location 70' and location 82' can be determined by calculating a line 92 that is tangent to posterior surface 60 at location 70' and a line 94 that is tangent to posterior surface 60' at location 82'. The angle, $\phi_1$, between tangent line 92 and tangent line 94 can then be calculated as a measure of the tilt component of the surface irregularity 80 at location 82'. Although FIG. 7 only shows a tilt angle, $\phi_1$ calculated in one plane, it is to be appreciated that more than one tilt angle for the location 82' may be calculated using the above-described method and used to compensate for tilt. For example a tilt angle, $\phi_{1,x}$ can be calculated in an x-z plane and compensated by steering the beam in an x direction and another tilt angle, $\phi_{1,y}$ can be calculated in an y-z plane and compensated by steering the beam in an y direction.

Figure 8:
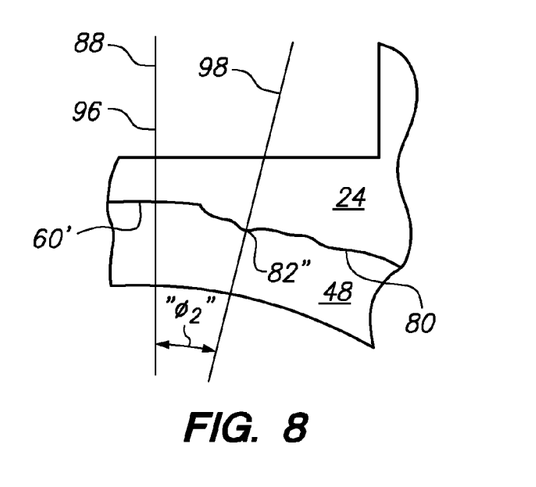
FIG. 8 is an enlarged detail view of a cornea of the eye and a patient interface having a surface irregularity as in FIGS. 6 and 7 illustrating the measurement of a tilt component of the surface irregularity, a normal axis for the tilt component and the comparison of the tilt component axis to an anatomical axis of the eye, such as the visual axis or the optical axis, for compensation purposes.

Alternatively, as shown in FIG. 8, an anatomical axis 96 of the eye such as the eye's optical axis or visual axis can be identified by processing image data and used for the reference datum 88. In particular, FIG. 8 shows that an axis 98 that is normal to the posterior surface 60 of the patient interface 24 at location 82" can be calculated by the computer system 34 (FIG. 1) and then compared with an anatomical axis 96 to calculate a tilt component of the surface irregularity 80. Specifically, as shown, an angle $\phi_2$, between the axis 98 and anatomical axis 96 can be calculated for the location 82". Although FIG. 8 only shows a tilt angle, $\phi_2$ calculated in one plane, it is to be appreciated that more than one tilt angle for the location 82" may be calculated using the above-described method and used to compensate for tilt. For example a tilt angle, $\phi_{2,x}$ can be calculated in an x-z plane and compensated by steering the beam in an x direction and another tilt angle, $\phi_{2,y}$ can be calculated in an y-z plane and compensated by steering the beam in an y direction.

Once the tilt is determined by either of the above described methods, Step 90 indicates that the computer system 34 (FIG. 1) can generate an output signal(s) that is indicative of the tilt(s) and transmit the output signal to the beam delivery system. The beam delivery system can then respond to the signal by moving a beam delivery system component, such as one or more optics in the scanning subsystem 14 by an appropriate increment that will compensate for the tilt component of the surface irregularity 80.

Figure 9:
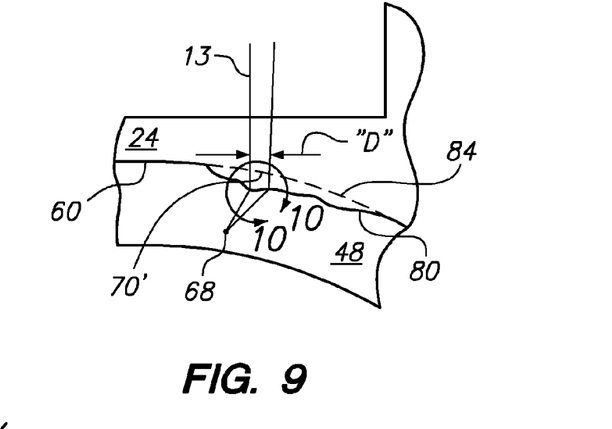
FIG. 9 is an enlarged detail view of a cornea of the eye and a patient interface having a surface irregularity as in FIGS. 6-8 illustrating the measurement of a surface profile deviation component of the surface irregularity and the comparison of the surface profile deviation component to a corresponding surface on a reference model for compensation purposes.

FIG. 4 also shows (Step 100) that the acquired image data can be compared to a reference datum 102 to characterize and compensate for a surface profile deviation of a surface irregularity 80 (see FIG. 9). Once characterized, the surface profile deviation can be used to generate an output signal for adjusting an adaptable optic 30 (FIG. 1) to compensate for the surface profile deviation (Step 104).

Figure 10:
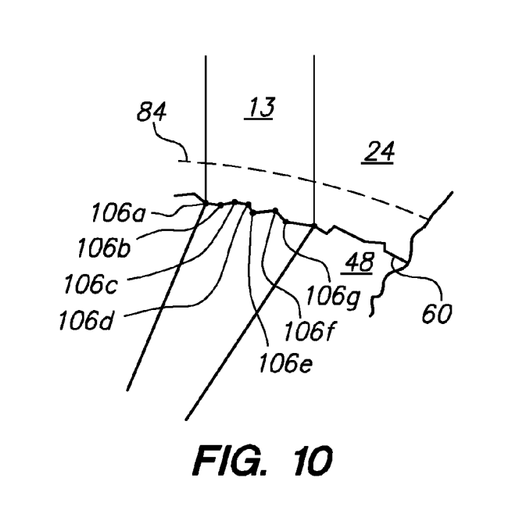
FIG. 10 is an enlarged detail view of a cornea of the eye and a patient interface having a surface irregularity as enclosed by detail line 10-10 in FIG. 9 illustrating a series of points on the surface irregularity, the coordinates of which can be processed by the computer system to determine a compensating adaptable optic configuration that will compensate for the surface profile deviation component of the surface irregularity.

FIGS. 9 and 10 illustrate an implementation for characterizing a surface profile deviation using a reference model surface 84 as the reference datum 102. As described above with reference to FIG. 6, the location 70' can be first ascertained as the position on the reference model surface 84 where a surgical laser beam 13 directed to location 68 would pass. In addition, FIG. 9 illustrates that the surgical laser beam 13 converges to a focal spot at the desired treatment location 68. As such, the surgical laser beam 13 has a diameter "D" at a location near the location 70' and establishes a substantially circular 'footprint' on the posterior surface 60 of the patient interface 24. As discussed above, the surface profile of this 'footprint', if irregular, can affect beam quality, in the absence of compensation.

FIG. 10 illustrates one technique for characterizing the surface profile. As shown, image data of the posterior surface 60 of the patient interface 24 where the beam will pass through can be divided into discrete sampling points (of which example sampling points 106a-g are labeled). The coordinates of the sampling points 106a-g are then determined relative to the reference model surface 84 and input to the computer system 34 (FIG. 1). It is to be appreciated that the posterior surface 60 can be sampled in two dimensions, rather than the single dimension shown.

Once acquired, the sampling points 106a-g can be used by the computer system 34 (FIG. 1) to construct a surface profile deviation for the surface irregularity 80 (FIG. 9). The surface profile deviation can then be used to estimate a wavefront profile that will be induced by the surface irregularity 80. A compensating signal can then be generated by the computer system 34 (FIG. 1) and sent to the beam delivery system (Step 104). For example, the compensating signal can be configured to cause the adaptive optic 30 (FIG. 1) of the beam delivery system to induce a wavefront profile on the beam that is equal and opposite to the estimated wavefront profile that will be induced by the surface irregularity 80 (FIG. 9).

More than one iteration of Step Sequences 74, 78, 86, 90, 100, 104 (FIG. 4) may be performed before firing the laser source 12 (FIG. 1) to increase accuracy. Once sufficient compensation has been obtained, the laser source 12 (FIG. 1) can be fired (Step 108) to produce LIOB at the location 68 (FIG. 5). FIG. 4 shows that when all LIOB of the locations on the path 66 (FIG. 5) has been completed (Step 110), the procedure can end (Step 112), otherwise, Step Sequence 74, 78, 86, 90, 100, 104 is performed (line 114) for a subsequent location on the path 66 (FIG. 5).

Additionally, the techniques described above for compensating for surface irregularities on an imagable surface (such as the posterior surface 60 of a patient interface 24 (FIGS. 5-10) can be combined with other closed loop systems designed to increase the positional accuracy when moving a focal spot along a path 66 (FIG. 5). Specifically, the above described techniques can be used in conjunction with the open loop and/or closed loop techniques described in U.S. Pat. No. 8,088,124, titled "System and Method for Precise Beam Positioning in Ocular Surgery," to Frieder Loesel, Mathias Glasmacher, and Ulrich von Pape, the entire contents of which are hereby incorporated by reference herein.

While the particular Dimensional Compensator for Use With a Patient Interface as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for directing a focal spot of a surgical laser beam to tissue in a treatment area of an eye during ocular surgery, with compensation for defects in laser beam position and quality caused by surface irregularities introduced during a manufacture of a patient interface, the apparatus comprising:
- a patient interface having a posterior surface;
- a beam delivery system including a scanning subsystem for guiding the surgical laser beam along a beam path through the patient interface and to a desired focal spot location in the treatment area;
- an optical detector for creating image data including data representing at least a portion of the posterior surface of the patient interface; and
- a computer system configured to receive image data from the optical detector and processing said image data to compare at least a portion of the posterior surface with a reference datum, wherein the reference datum is a computer model of a posterior surface of a patient interface having no surface irregularities, to calculate a z-axis deviation from the reference datum and a tilt deviation from the reference datum for the posterior surface of the patient interface due to irregularities of the posterior surface of the patient interface, and to generate an output signal to adjust the scanning subsystem in order to compensate for defects in laser beam position caused by the posterior surface irregularities of the patient interface.

2. An apparatus as recited in claim 1 wherein the optical detector creates image data representing the treatment area.

3. An apparatus as recited in claim 1 wherein the computer system processes the image data to identify an axis for the posterior surface and an anatomical axis for the eye as the reference datum and wherein the computer system compares the posterior surface axis to the anatomical axis to calculate patient interface tilt.

4. An apparatus as recited in claim 3 wherein the anatomical axis is the visual axis of the eye.

5. An apparatus as recited in claim 3 wherein the anatomical axis is the optical axis of the eye.

6. An apparatus as recited in claim 1 wherein the beam delivery system includes a focusing optic movable along a z-axis and wherein the computer system is adapted to process said image data to identify a z-axis coordinate where the beam passes through the posterior surface and compares the identified coordinate to a corresponding coordinate on the computer model of the patient interface surface having no surface irregularities to calculate a difference, $\Delta z$, the computer system adapted to output a signal to the beam delivery system indicative of the difference, $\Delta z$, to move the focusing optic and compensate for a z-axis deviation of the posterior surface irregularity.

7. An apparatus as recited in claim 1 wherein the optical detector is selected from the group of optical detectors consisting of an optical coherence tomography (OCT) detector, a confocal imaging detector, a Scheimpflug principle imaging detector, a two photon imaging detector and a second harmonic generation imaging detector.

8. An apparatus as recited in claim 1 wherein the posterior surface of the patient interface is sized and shaped to conform to the exterior surface of the cornea of the eye.

9. An apparatus as recited in claim 1 wherein the patent interface has an anterior surface and a posterior surface, and wherein each surface irregularity on the anterior surface and on the posterior surface is individually and separately compensated for.

10. An apparatus as recited in claim 1 wherein a same reference datum is used for calculating the z-axis deviation and the tilt deviation.

* * * * *